US012715801B2

(12) United States Patent
Dreyer et al.

(10) Patent No.: US 12,715,801 B2
(45) Date of Patent: Aug. 25, 2026

(54) EXTENDED- AND MULTIMODAL-RELEASE COMPOSITIONS

(71) Applicant: Finoric, LLC, Beasley, TX (US)

(72) Inventors: Daniel R. Dreyer, Rosenberg, TX (US); Pious Kurian, Sugar Land, TX (US); Ambrish Kamdar, Sugar Land, TX (US)

(73) Assignee: Finoric LLC, Beasley, TX (US)

( * ) Notice: Subject to any disclaimer, the term of this patent is extended or adjusted under 35 U.S.C. 154(b) by 0 days.

(21) Appl. No.: 18/909,730

(22) Filed: Oct. 8, 2024

(65) Prior Publication Data

US 2025/0136488 A1 May 1, 2025

Related U.S. Application Data

(60) Provisional application No. 63/594,464, filed on Oct. 31, 2023.

(51) Int. Cl.

| | |
|---|---|
| ***C02F 5/14*** | (2023.01) |
| ***C07C 229/16*** | (2006.01) |
| ***C07F 9/38*** | (2006.01) |
| ***C09K 8/528*** | (2006.01) |
| ***C09K 8/68*** | (2006.01) |
| ***C09K 8/80*** | (2006.01) |
| ***E21B 37/06*** | (2006.01) |

(52) U.S. Cl.
CPC ............ *C02F 5/145* (2013.01); *C07C 229/16* (2013.01); *C07F 9/3895* (2013.01); *C09K 8/528* (2013.01); *C09K 8/68* (2013.01); *C09K 8/80* (2013.01); *E21B 37/06* (2013.01)

(58) Field of Classification Search
None
See application file for complete search history.

(56) References Cited

U.S. PATENT DOCUMENTS

| | | | | |
|---|---|---|---|---|
| 2011/0028358 | A1* | 2/2011 | Welton .................... | C09K 8/03 507/236 |
| 2023/0235213 | A1* | 7/2023 | Parravicini ........... | C09K 8/528 166/311 |
| 2023/0322977 | A1* | 10/2023 | Dawson ................. | C08F 22/38 524/428 |

* cited by examiner

*Primary Examiner* — Andrew Sue-Ako

(57) ABSTRACT

Disclosed herein are extended- and multimodal-release compositions for inhibiting scale in an industrial water system. In an example, an extended-release composition for inhibiting scale in an industrial water system includes a solid, particulate scale inhibitor. The solid, particular scale inhibitor may include a phosphonate, a carboxylate, or a combination thereof; and a divalent cation, a trivalent cation, or a combination thereof. In some cases, the solid, particulate scale inhibitor is substantially free of an inert material

19 Claims, 5 Drawing Sheets

Na+ Na+ Na+ Na+

$MX_y$

*where m is a polyvalent cation*

+ NaX (aq.)

FIG. 1

EXTENDED- AND MULTIMODAL-RELEASE COMPOSITIONS

FIELD

Disclosed herein are extended-release compositions and multimodal-release compositions for inhibiting scale in an industrial water system.

BACKGROUND

Mineral scale occurs commonly in an industrial water system (e.g., oilfield environments), as it does in other environments where changes in water pressure, temperature, and/or composition result in the deposition of insoluble inorganic salts. Calcite ($CaCO_3$) and barite ($BaSO_4$) are the most common forms seen in subterranean conditions, but other forms of scale (e.g., magnesite, siderite, gypsum, iron sulfide, etc.) can also occur. Mineral scale deposition is one of the top three problems associated with petroleum recovery. Zhang (2020).

A wide range of chemical scale inhibitors, dispersants and remediation agents have been developed over the course of decades of study and optimization. While effective, these chemistries have an inherently limited period of efficacy. This is largely driven by the fact that as water is produced from the well alongside the desired oil and gas, the scale inhibitor flows out with the aqueous phase. Eventually the concentration of the inhibitor falls below a critical level (the so-called "minimum inhibitor concentration" or "MIC"), and at this point scale formation is no longer controlled and deposition will begin to occur. Fouling can occur within the geological formation itself, in the various tubulars of the well (e.g., well casing), or in surface equipment (e.g., pumps, valves, etc.). To mitigate this fouling, inhibitors are commonly applied continuously, or in periodic slugs (squeeze treatments). However, this kind of chemical treatment can be quite expensive both in terms of the costs of the inhibitor itself, as well as the equipment needed to deliver the inhibitor downhole. Additionally, topside treatments may not be able to reach deep into the fractures of a formation; if scale forms in these areas, it may be impossible to remove, and those portions of the well will no longer contribute to the overall production of the well. To that end, there is value in injecting scale inhibitors that are released for a prolonged period (weeks, months, or conceivably even longer). Typically, these are solid products that can be easily applied deep into the formation during well completion alongside other solids (e.g., proppant). As these products slowly release the active inhibitor, scale deposition can be inhibited beginning at the early stages of a well's lifetime, delaying the need for conventional scale treatments. Protection against scaling will persist as long as the concentration of the inhibitor remains above the MIC, which is a function of both the rate of release of the active inhibitor from the product and the overall amount of product injected into the well.

Various slow-release products have been developed and commercialized over the years. Typically, these are encapsulated products where an active's dissolution into aqueous media is controlled by the presence of an external coating material. Variation of the composition of the coating material and thickness can be used to control the release rate. There are also descriptions of sparingly soluble scale inhibitors (e.g., polyphosphates) and the deposition of sparingly soluble inhibitors onto inorganic substrates (adsorbents). However, there appears to be a critical gap in the technology that has been described herein. There are certain types of agents (e.g., aminocarboxylates, aminophosphonates) that are particularly useful for the control of multiple types of scale and are widely used for scale inhibition in many different industries. Moreover, these agents can be rendered sparingly soluble by mixing a soluble form of the active molecule (e.g., $Na^+$ or $K^+$ salts, or the acids themselves) with a soluble form of a precipitating counterion (e.g., $Ca^{2+}$ or $Mg^{2+}$). The resulting compositions display inherent slow-release properties that can be useful in subterranean applications where slow release of the active inhibitor may be desirable. Formation of an inherently sparingly soluble material obviates the need for a supporting/carrier substrate or additional treatments (e.g., encapsulation) to reduce dissolution rate, although the latter can optionally be performed to further slow the release rate of the active molecule.

The use of sparingly soluble compositions in industrial water systems, including subterranean oilfield applications for scale control, has not been described.

SUMMARY

Disclosed herein are extended-release compositions and multimodal-release compositions for inhibiting scale in an industrial water system where the multimodal-release can be modulated by varying the compositional makeup of scale inhibitor. By applying sparingly soluble salts of anionic scale inhibitors during completion of a well, it is possible to prevent scale formation for a prolonged period after completion is finished. Most scale inhibitors are readily soluble in aqueous media and thus are readily released (produced) from the well, even if applied at high dosage. Conversely, sparingly soluble salts will release far more slowly, allowing for extended periods of protection against common oilfield scales (e.g., calcite, barite).

BRIEF DESCRIPTION OF THE DRAWINGS

FIG. 1. Reaction scheme for preparing the sparingly soluble compositions described herein from readily soluble precursors. $Na_4EDTA$ is used as a representative example, but other polycarboxylates (e.g., NTA) or polyphosphonates (e.g., ATMP, DTPMP, etc.) may be substituted, where the "R" moiety may be a polycarboxylate, a polyphosphonate, and the like).

DETAILED DESCRIPTION

Figure 2:
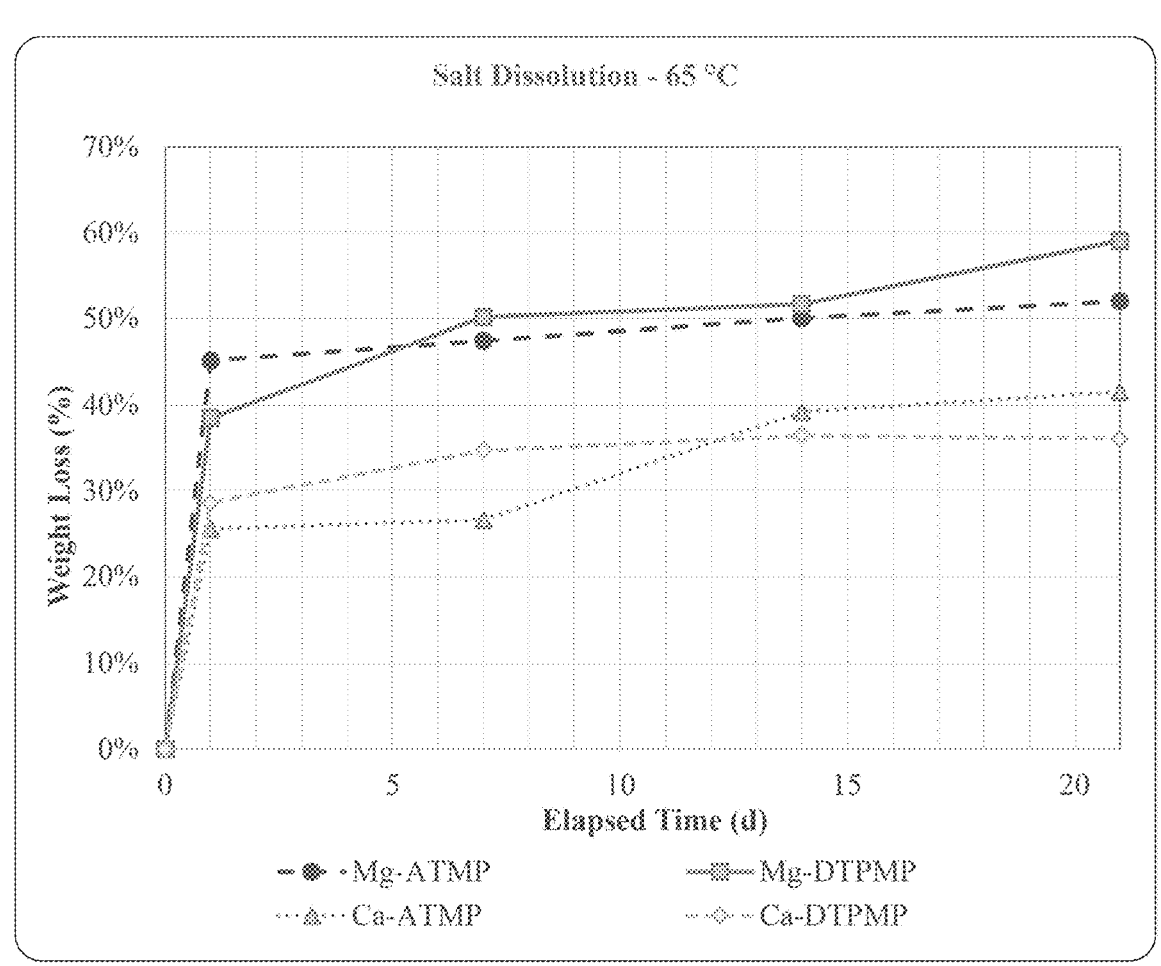
FIG. 2. Dissolution of $Ca^{2+}$ and $Mg^{2+}$ salts of ATMP and DTPMP in deionized water at 65° C.

The information that follows describes embodiments with reference to the accompanying figures, in which preferred embodiments may be shown. The foregoing may, however, be embodied in many different forms and should not be construed as limited to the illustrated embodiments set forth herein.

The use of the terms “a” and “an” and “the” and similar references in the context of describing the compositions disclosed herein (especially in the context of the claims) are to be construed to cover both the singular and the plural, unless otherwise indicated herein or clearly contradicted by context. For example, an agent refers to one or more agents or at least one agent. As such, the terms “a” (or “an”), “one or more”, and “at least one” can be used interchangeably herein. The use of the definite article (“the”) to refer to “an entity” refers to one or more of that entity. For example, when the expression “the agent” refers to the previously recitation of “an agent” it is understood that the expression “the agent” refers to one or more agents, unless context indicates otherwise.

The terms “optional,” “optionally,” “if applicable,” or “if present” as used herein means that a subsequently described element, event, or circumstance may but need not occur, and that the description includes instances where the event or circumstance occurs and instances in which it does not.

Recitation of ranges of values herein are not intended to be limiting, referring instead individually to any and all values falling within the range, unless otherwise indicated herein, and each separate value within such a range is incorporated into the specification as if it were individually recited herein.

It may be appreciated that a numerical value recited herein may be associated with a standard variation, such as ±5%, ±1%, or ±0.2%. The words “about,” “approximately,” or the like (e.g., ≈), when accompanying a numerical value, are to be construed as indicating a deviation as would be appreciated by one of ordinary skill in the art to operate satisfactorily for an intended purpose. A stated amount for a compositional ingredient that is not preceded by the term “about” (or the like) does not mean that there is no variance for the stated term, as one of ordinary skill would understand that there is always some possibility of a degree of variability generally associated with experimental error.

Ranges of values and/or numeric values are provided herein as examples only, and do not constitute a limitation on the scope of the described embodiments. The use of any and all examples, or exemplary language (“e.g.,” “such as,” or the like) provided herein, is intended merely to better illuminate the embodiments and does not pose a limitation on the scope of the embodiments or the claims. No language in the specification should be construed as indicating any unclaimed element as essential to the practice of the embodiments.

Percents disclosed herein relate to weight-% (wt %) based on the total weight of the composition, unless otherwise indicated.

The expression “pptg” refers to the amount of material in pounds of solid per thousand gallons of fluid.

Extended-Release Composition for Inhibiting Scale in an Industrial Water System

An embodiment disclosed herein relates to an extended-release composition for inhibiting scale in an industrial water system, comprising: a solid, particulate scale inhibitor (“SPSI”) comprising: a phosphonate, a carboxylate, or a combination thereof and a divalent cation, a trivalent cation, or a combination thereof; wherein the solid, particulate scale inhibitor is substantially free of an inert material.

In one aspect, the extended-release composition may be used for inhibiting scale in an industrial water system, such as, one or more of a subterranean formation (e.g., hydraulically generated fractures of a wellbore), a heat exchanger, a cooling tower, a pipeline, a water softener system, a waste water treatment system, a paper mill, a mining system, a geothermal system, a fluid cooling system, a water treatment system, a water purification system, a wastewater treatment system, a reverse osmosis membrane, an ultrafiltration system, a water storage system, or an ion exchanger. It may be appreciated that the SPSI may be used for inhibiting scale in hydraulic fracturing treatment of an oil or gas well.

The SPSI disclosed herein may be characterized based on its solubility, dissolution rate, or a combination thereof.

With respect to SPSI solubility, the SPSI may be partially soluble in water where the parts of water required to dissolve the SPSI may be greater than or equal to 100, such as, for example, the parts of water required to dissolve the SPSI may be 100, 1,000, 10,000, 100,000, 1,000,000, and the like. To be clear, 1 part of SPSI may dissolve in 1,000 parts of water, where a part may be any suitable mass unit, such as, milligrams (mg), grams (g), kilogram (kg), and the like. One will appreciate that the solubility of the SPSI disclosed herein relates generally to the solubility of the SPSI in water with no added solutes (e.g., purified water). Generally, industrial water systems may not comprise purified water, but may include one or more solutes (e.g., salts, particulate inorganic matter, and/or organic matter). Accordingly, one will appreciate that the parts of water required to dissolve the SPSI may differ from the parts of industrial water required to dissolve the SPSI. Therefore, the stated parts of water required to dissolve the SPSI is not meant to limit the amount of industrial water required to dissolve the SPSI.

With respect to SPSI dissolution rate, one will appreciate that the SPSI may be introduced into an industrial water system and the release-rate (e.g., dissolution) into the surrounding aqueous environment may be governed by the SPSI's variable solubility. Conceptually, the extended-release composition may slowly release the SPSI in the industrial water system such that scale-inhibition occurs over an extended period, such as about one-month, about 3-months, about 6-months, about 9-months, about 12-months, or more.

Examples of phosphonates include a partially or fully deprotonated form of the respective polyphosphonic acid (with CAS Registry No.), including, for example, 1-hydroxyethylidene-(1,1-diphosphonic acid) (HEDP, 2809-21-4); aminobis(methylene-phosphonic acid) (methylene-phosphonic acid) (ABMP, 17261-34-6); methyliminobis (methylenephosphonic acid) (MIBMP, 5995-25-5); aminotrimethylenephosphonic acid (ATMP, 6419-19-8); diethylenetriamine-penta(methylenephosphonic acid) (DTPMP, 15827-60-8); ethylenediaminetetra(methylene phosphonic acid) (EDTMP, 1429-50-1); bis(hexamethylenetriaminepenta(methylenephosphonic acid)) (BHMTPMP, 34690-00-1); aminoethylethanolamine (AEEA) phosphonic acid (or its salts thereof), also referred to as N-hydroxyethyl (ethylenediamine)-N,N',N'-tri(methylene phosphonic acid) (HEDTMP) ($C10H28N2O12P4$); and the like. In one aspect, the extended-release composition excludes the free acid form of the phosphonate.

Examples of carboxylates include a partially or fully deprotonated form of the respective polycarboxylic acid (with CAS Registry No.), including, for example, citric acid (77-92-9); isocitric acid (320-77-4); aconitic acid (499-12-7); 1,3,4-propanetricarboxylic acid (99-14-9); dihydroxymaleic acid (526-84-1); 1,2-Diaminocyclohexane-N,N,N',N'-tetraacetic acid (DCyTA, 482-54-2); ethylenediaminetetraacetic acid (EDTA, 60-00-4); diethylenetriaminepentaacetic acid (DETPA, 67-43-6); nitrilotriacetic acid (NTA, 139-13-9); iminodiacetic acid (IDA, 142-73-4); hydroxyethylethylenediaminotriacetic acid (HEDTA, 150-39-0); ethylenediamine-N,N'-disuccinic acid (EDDS, 20846-91-7); methyglycine diacetic acid (MGDA, 29578-05-0); (2-hydroxyethyl)iminodiacetic acid (HEIDA, 93-62-9); glutamic acid-N,N-diacetic acid (GLDA, 58976-65-1); ethylenediaminedi-o-hydroxyphenylacetic acid (EDDHA, 1170-02-1); N-methyliminodiacetic acid (MIDA, 4408-64-4); iminodisuccinic acid (IDS, 7408-20-0); 1,2-diaminopropane-N,N,N',N'-tetraacetic acid (MeEDTA, 4408-81-5); N-(2-acetamido)iminodiacetic acid (ADA, 26239-55-4); N-(2-carboxyethyl)iminodiacetic acid (6245-75-6); L-aspartic acid-N,N-di(acetic acid) (ASDA, 24868-49-3); N-(carboxymethyl)-L-aspartic acid (41035-84-1); strombine (56857-47-7); hydroxyiminodisuccinic acid (194604-51-8); N-(carboxymethyl)aspartic acid (56375-41-8); N-bis[2-(1,2-dicarboxyethoxy)ethyl] glycine (244028 September 9); N,N'-1,3-propanediylbis(aspartic acid) (193207-34-0); 1,6-hexamethylenediamine N,N'-disuccinic acid (687-34-3); 2,2',2"-[nitrilotris(2,1-ethanediyloxy)]tris[butanedioic acid] (199874-61-8); N-(carboxymethyl)-N-(hydroxymethyl)glycine (33454-80-7); 1,3-diamino-2-hydroxypropane-N,N'-disuccinic acid (193207-51-1); N-(2-carboxyethyl)aspartic acid (153352-57-9); N,N-bis[2-(1,2-dicarboxyethoxy)ethyl] aspartic acid (205699-22-5); N,N'-(iminodi-2,1-ethanediyl) bis(aspartic acid) (52759-68-9); 2,16-bis(carboxymethyl)-3,6,9,12,15-pentaazaheptadecanedioic acid (687-36-5); 3,6,9,12-tetraazatetradecane-1,2,13,14-tetracarboxylic acid (687-35-4); N,N'-(1-methyl-1,2-ethanediyl)bis(aspartic acid) (200942-89-8); N,N-bis(carboxymethyl)-3-sulfo-L-alanine (146453-14-7); N-(carboxymethyl)-3-sulfo-L-alanine (17929-83-8); 2,13-bis(carboxymethyl)-6,9-dioxa-3,12-diazatetradecanedioic acid (200943 July 3); N-(3-carboxy-3-hydroxy-1-oxopropyl)-L-aspartic acid (1373550-84-5); 2,2'-[[(1-carboxyethyl)imino]bis(2,1-ethanediyloxy)]bis [butanedioic acid] (919782-10-8); N-[(1S)-1-carboxy-2-hydroxyethyl]-3-hydroxyaspartic acid (1647047-58-2); and N,N'-cyclohexanediylbis(aspartic acid) (1708967-70-7). In one aspect, the extended-release composition excludes the free acid form of the carboxylate.

SPSIs contemplated herein may include a mixed-phosphonate/carboxylate or a polymer. Examples of mixed-phosphonate/carboxylates include a partially or fully deprotonated form of the respective mixed-phosphonic/carboxylic acid, such as 2-carboxyethyl phosphonic acid (CEPA); 2-Hydroxyphosphonocarboxylic acid (HPAA); N,N-bis (phosphonomethyl)glycine (BPMG); N-(phosphonomethyl) iminodiacetic acid (PMIDA); Phosphonobutanetricarboxylic acid (PBTC); 2-Phosphonobutane-1,2,4-tricarboxylic acid (PBTC, 37971-36-1); 2-Hydroxy phosphonoacetic acid (HPAA, 23783-26-8); (2-Phosphono butane-1,2,4-tricarboxylic acid (PBTCA, 37971-36-1); N-(Phosphonomethyl)glycine (1071-83-6); N-(phosphonomethyl)iminodiacetic acid ($H_2O_3PCH_2N(CH_2CO_2H)_2$ ($H_4$PMIDA); 1,4,7-triazacyclononane-N,N',N"-trimethylene phosphonic acid (H6NOTP); 1,4,7-triazacyclononane-N-methylenephosphonic acid-N',N"-dimethylenecarboxylic acid (H4NO2AP); 1,4,7-triazacyclononane-N,N'-bis(methylene-phosphonic acid)-N"-methylene carboxylic acid (H5NOA2P). In one aspect, the extended-release composition excludes the free acid form of the mixed-phosphonate/carboxylate.

Examples of a polymer include a partially or fully deprotonated form of the respective polymeric acid, such as, polyvinylphosphonic acid (27754-99-0); polyacrylic acid (9003-01-4); polymethacrylic acid (25087-26-7); polyphosphinocarboxylic acid (PPCA, 2865832-79-5); and the like. In one aspect, the extended-release composition excludes the free acid form of the polymer.

In one aspect of the extended-release composition for inhibiting scale in an industrial water system, the solid, particulate scale inhibitor is substantially free of an inert material, where substantially free of an inert material means that the SPSI includes no more than about 10% of inert material, no more than about 5% of inert material, no more than about 1% of inert material, no more than about 0% inert material, and no more than 0% inert material (e.g., the SPSI excludes the inert material).

The expression "inert material" relates generally to a material that does not function as a scale inhibitor. An inert material may include an inert support material (e.g., inorganic or organic), an inert coating material (e.g., inorganic or organic), or a combination thereof. Examples of inert support materials include, for example, diatomaceous earth, activated carbon, silica (e.g., silica particulate), precipitated silica, zeolite, ground nut shells (e.g., walnut, pecan, peanut, and the like), Fuller's earth, a polymeric material, or an organic synthetic high molecular weight water-insoluble adsorbent. Examples of inert coating materials include, for example, a polyolefin, a polyester, a polyamide, a polycarbonate, a polyacetal, a polymelamine, a polyvinyl chloride, a polyvinylidene dichloride, a polyvinyl acetate, a polyvinyl ester, a polyacrylic acid, a bisphenol, an isocyanate, or blends thereof, including, for example, ethylene vinyl acetate, polylactic acid, a product of phthalic anhydride and ethylene vinyl acetate, a mixture comprising ethylene vinyl acetate and a plasticizer (e.g., dioctyl phthalate).

In another aspect, the SPSI comprises at least 1 wt % of a divalent cation, a trivalent cation, or a combination thereof. Examples of di- and trivalent cations include isotopically stable elements from the periodic table of the elements from Groups 2 to 13, a protonated organic diamine (e.g., ethylenediamine, diaminobenzene (e.g., o-phenylenediamine, m-phenylenediamine, p-phenylene diamine), triamine (e.g., 1,2-3-triaminopropane), or combinations thereof. Examples of divalent cations include, but are not limited to, divalent calcium ($Ca^{2+}$), divalent magnesium ($Mg^{2+}$), divalent zinc ($Zn^{2+}$). Examples of trivalent cations include, but are not limited to, trivalent aluminum ($Al^{3+}$), trivalent cobalt ($Co^{3+}$), trivalent lanthanum ($La^{3+}$).

One will appreciate that the weight-amount of a divalent cation, a trivalent cation, or a combination thereof is not without an upper bound. For instance, one will appreciate the weight-amount of divalent cation will depend on the weight amount and total charge of, for example, phosphonate, such that a stoichiometric amount cationic species will be present in the SPSI. Thus, if the polyphosphonate has a negative charge of 6, then the scale inhibitor comprises 3-mole equivalents of a divalent cation, such that the mole ratio of divalent cation to polyphosphonate is 3.

One also will appreciate that the SPSI may further comprise an amount of monovalent cation ("MVC") in addition to the divalent cation ("DVC") and/or trivalent cation ("TVC"). As explained herein, a solid scale inhibitor may be obtained from a readily aqueous soluble phosphonate, carboxylate, or a combination thereof. As an example, aminotrimethylenephosphonic acid (ATMP) may be utilized as a potassium salt (e.g., $K_6$ATMP) for the preparation of a solid scale inhibitor ("SSI") comprising a DVC (e.g., $Ca^{2+}$). It will be appreciated that completely deprotonated ATMP includes three anionic phosphonate moieties providing a net negative charge of six. Accordingly, the solid scale inhibitor comprising ATMP may comprise 2 MVCs and 2 DVCs (e.g., $K_2Ca_2$ATMP). Using $K_2Ca_2$ATMP as an example, one may readily calculate the amount of MVC present in the SSI, as well as the solid, particulate scale inhibitor (aka, SPSI). For illustrative purposes only, the molar mass of completely deprotonated ATMP ($C_3H_6O_9P_3$) is about 279 g/mol, while the molar mass of $K_2Ca_2$ATMP ($K_2Ca_2C_3H_6O_9P_3$) is about 437.35 g/mol, which provides an amount of MVC (e.g., $K^+$) of about 17.9 wt % and an amount of DVC (e.g., $Ca^{2+}$) of about 18.3 wt % of the SSI. It will be appreciated that the stoichiometric amounts of MVC, DVC, and TVC relative to the phosphonate and/or carboxylate may be used to calculate the amount of each of MVC, DVC, and TVC. As another example, diethylenetriamine-penta(methylenephosphonic acid) (DTPMP), when completely deprotonated includes five anionic phosphonate moieties providing a net negative charge of ten, and thus, one may contemplate variations of DTPMP, such as $(MVC)_2(DVC)_4$DTPMP (e.g., $K_2Ca_4$DTPMP ($K_2Ca_4C_9H_{18}O_{15}P_5$) with a molar mass of about 604.74, a potassium amount of about 12.9 wt %, and a calcium amount of about 26.5%); $(MVC)(TVC)_3$DTPMP (e.g., $KAl_3$DTPMP ($KAl_3C_9H_{18}O_{15}P_5$) with a molar mass of about 641.14 g/mol, a potassium amount of about 6.1 wt %, and an aluminum amount of about 12.6 wt %); and the like. The same exercise may be performed for a partially deprotonated phosphonate and/or carboxylate where the MVC is $H^+$ and the solid scale inhibitor comprises a DVC, a TVC, or a combination thereof. In view of the foregoing, the SPSI may further comprise at least 1 wt % of a monovalent cation with the understanding that the upper limit amount of monovalent cation does not alter the extended-release property of the extended-release composition for inhibiting scale in an industrial water system.

In another aspect, the SPSI comprises at least 1 wt % of divalent magnesium, divalent calcium, or a combination thereof.

In one aspect, the extended-release composition for inhibiting scale in an industrial water system, the SPSI has a particle size of from about 10 to about 100, with specific values of about 20 mesh, about 30 mesh, about 35 mesh, about 40 mesh, about 45 mesh, about 50 mesh, about 60 mesh, about 80 mesh, and about 100 mesh.

Process for Preparing the Extended-Release Composition

Another embodiment disclosed herein relates to a process for preparing the extended-release composition for inhibiting scale in an industrial water system, comprising: a solid, particulate scale inhibitor ("SPSI") comprising: a phosphonate, a carboxylate, or a combination thereof and a divalent cation, a trivalent cation, or a combination thereof, said process comprising: reacting a readily aqueous soluble phosphonate, carboxylate, or a combination thereof with a readily aqueous, soluble metal salt comprising a divalent cation, a trivalent cation, or a combination thereof to obtain a solid scale inhibitor (SSI).

In contrast to the SPSI disclosed herein exhibiting partial solubility in water, a readily aqueous soluble reagent (e.g., phosphonate, carboxylate, or combination thereof) dissolves rapidly in water. For instance, a readily soluble reagent dissolves readily in a smaller amount of water, including, for example, one part of readily soluble reagent dissolves in: (i) less than about 100 parts of water, (ii) less than about 30 parts of water, (iii) less than about 10 parts of water, and (iv) less than about 1 part of water. In one aspect, the readily aqueous soluble reagent dissolves in less than about 1 part of water.

In one aspect of the process for preparing the extended-release composition for inhibiting scale in an industrial water system, said process may further comprise reacting a suitable phosphonic acid, carboxylic acid, etc. with a suitable amount of a basic agent, such as a hydroxide-containing salt (e.g., NaOH, KOH, or a combination thereof), a carbonate (e.g., $NaHCO_3$, $KHCO_3$, $Na_2CO_3$, $K_2CO_3$, and the like), ammonia (either aqueous or anhydrous), to obtain the readily aqueous soluble phosphonate, carboxylate, or a combination thereof.

In one aspect of the process for preparing the extended-release composition for inhibiting scale in an industrial water system, the SSI may be ground to obtain the SPSI having a particle size of from about 20 to about 100, with specific values of about 20 mesh, about 30 mesh, about 35 mesh, about 40 mesh, about 45 mesh, about 50 mesh, about 60 mesh, about 80 mesh, and about 100 mesh.

In one aspect of the process for preparing the extended-release composition for inhibiting scale in an industrial water system, the SSI may be ground to obtain the SPSI having a particle size of at least 100 mesh.

Method for Inhibiting Scale Formation Using Extended-Release Composition

The extended-release composition disclosed herein may be included along with a proppant during hydraulic fracturing, including, for example in a horizontal well, or a vertical well.

Accordingly, another embodiment disclosed herein relates to a method for inhibiting scale formation in a subterranean formation, the method comprising mixing the extended-release composition disclosed herein with a stimulation composition comprising a stimulation fluid and optionally one or more proppants to form a stimulation mixture and injecting the stimulation mixture under pressure into hydraulically generated fractures of a wellbore.

One will appreciate that the presence or absence of one or more proppants may depend on the status of the well. For instance, the stimulation mixture may include one or more proppants during the formation of a hydraulically fractured well system. Further, the stimulation mixture may exclude one or more proppants in the instance when one seeks to inhibit scale for previously fractured well.

In one aspect, the stimulation composition comprises one or more proppants and the stimulation mixture of the method for inhibiting scale formation in a subterranean formation comprises from about 0.01% to about 5% of the SPSI based on the weight of the proppant and all values in between including, for example, about 0.1%, about 1%, about 2%, about 3%, and about 4%.

In another aspect, the stimulation mixture comprises (or consists of) from about 0.001 pptg to about 5 pptg of the SPSI based on the volume of the stimulation fluid, including, for example, about 0.01 pptg, about 0.1 pptg, about 0.5 pptg, about 1 pptg, about 2 pptg, about 3 pptg, and about 4 pptg. In one aspect, the stimulation mixture comprises (or consists of) from about 0.01 pptg to about 1 pptg of the SPSI based on the volume of the stimulation fluid.

In yet another aspect of the method for inhibiting scale formation in a subterranean formation, the stimulation mixture may further comprise one or more of a corrosion inhibitor, a paraffin inhibitor, a salt formation inhibitor, a gas hydrate inhibitor, an asphaltene inhibitor, an asphaltene dispersant, a defoamer, an oxidizer, an oxygen scavenger, a biocide, a foaming agent, an emulsion breaker, and a surfactant.

Another embodiment disclosed herein relates to a method for inhibiting scale formation, the method comprising mixing the extended-release composition disclosed herein with an aqueous fluid to obtain a scale inhibiting composition and adding the scale inhibiting composition to the system to inhibit scale formation on a surface of the system which is in contact with the fluid.

In one aspect of the method for inhibiting scale, the surface of the system is within a heat exchanger, a cooling tower, a pipeline, a water softener, a wastewater treatment system, a paper mill, a mining system, a geothermal system, a fluid cooling system, a water treatment system, a water purification system, a wastewater treatment system, a reverse osmosis membrane, an ultrafiltration system, a water storage system, or an ion exchanger.

Multimodal-Release Composition

Another embodiment disclosed herein relates to a multimodal-release composition comprising a solid, particulate scale inhibitor ("SPSI") comprising: a phosphonate, a carboxylate, or a combination thereof and a divalent cation, a trivalent cation, or a combination thereof; and a second solid, particulate scale inhibitor ("SSPSI") comprising a phosphonate, a carboxylate, or a combination thereof and a monovalent cation.

The SPSI and SSPSI of the multimodal-release composition may be contrasted based on solubility, dissolution rate, or a combination thereof. The SPSI solubility and/or dissolution rate is described above. The SSPSI differs from the SPSI with respect to solubility and/or dissolution rate.

As related to SSPSI solubility, the SSPSI may be readily soluble in water where the parts of water required to dissolve the SSPSI is less than 100, less than 50, less than 30, less than 10, or even less than 1. To be clear, 1 part of SPSI may dissolve in less than 1,000 parts of pure water, where a part may be any suitable mass unit, e.g., mg, g, kg, etc. One will appreciate that the solubility of the SSPSI disclosed herein relates generally to the solubility of the SSPSI in water with no added solutes (e.g., purified water). Generally, industrial water systems may not comprise purified water, but may include one or more solutes (e.g., salts, particulate inorganic matter, and/or organic matter). Accordingly, one will appreciate that the parts of water required to dissolve the SSPSI may differ from the parts of industrial water required to dissolve the SSPSI. Therefore, the stated parts of water required to dissolve the SSPSI is not meant to limit the amount of industrial water required to dissolve the SSPSI.

With respect to SSPSI dissolution rate, one will appreciate that the SSPSI may be introduced into an industrial water system and readily dissolve in the industrial water system. Indeed, the dissolution rate of the SSPSI may be much greater than the dissolution rate of the SPSI, and thus, providing a multimodal-release profile for scale inhibition. For instance, the SSPSI may dissolve at a rate that is at least about 1,000-times (or more, e.g., 10,000-times) the dissolution rate of the SPSI. As an example, if the SSPSI dissolves in water in about 60-seconds, the SPSI may dissolve in about 17-hours. Alternatively, if the SSPSI dissolves in water in about 360-seconds, the SPSI may dissolve in about 100-hours. Conversely, if the SPSI dissolves in water in about 6-months (about 4,320-hours), the SSPSI may dissolves in water in about 4.3-hours. The multimodal-release profile may include a dual-release profile for scale inhibition. Alternatively, the multimodal-release profile may include three (or more) release profiles for scale inhibition.

One will appreciate that the solubility of the SSPSI disclosed herein relates generally to the solubility of the SSPSI in water with no added solutes (e.g., purified water). Generally, industrial water systems may not comprise purified water, but may include one or more solutes (e.g., salts, particulate inorganic matter, and/or organic matter). Accordingly, one will appreciate that the parts of water required to dissolve the SSPSI may differ from the parts of industrial water required to dissolve the SSPSI. Therefore, the stated parts of water required to dissolve the SSPSI is not meant to limit the amount of industrial water required to dissolve the SSPSI.

The exemplary listings of phosphonates, carboxylates, mixed-phosphonate/carboxylates, and polymers mentioned above may be utilized for the SSPSI, and in certain applications, the free acid may be used.

The relative amounts of the SPSI and SSPSI in the multimodal-release composition may vary to a degree to provide a multimodal-release profile. For instance, the scale inhibitor may comprise from about 5 wt % to about 99 wt % of SPSI with the remainder being the SSPSI. As an example, the multimodal-release composition may comprise about 20 wt % SSPSI and about 80 wt % SPSI, where the wt % is based on the total amount of SSPSI and SPSI. In another example, the multimodal-release composition may comprise about 50 wt % SSPSI and about 50 wt % SPSI, where the wt % is based on the total amount of SSPSI and SPSI. The SPSI and SSPSI may be a physical admixture obtained by, for example, mixing SPSI and SSPSI in a suitable blender or by melting each of the SPSI and SSPSI to obtain extruded product, which may be granulated using a suitable method.

In one aspect of the multimodal-release composition, each of the SPSI and SSPSI is substantially free of an inert material, where substantially free of an inert material means that the SPSI and/or SSPSI includes no more than about 10% of inert material, no more than about 5% of inert material, no more than about 1% of inert material, and about 0% inert material. Examples of inert materials are disclosed herein.

In one aspect of the multimodal-release composition, the SPSI has a water solubility of about 10,000 or less compared to the SSPSI. The water in this aspect may be purified water or industrial water.

In another aspect of the multimodal-release composition, the SPSI has a dissolution rate in water of about 1,000 or less compared to the SSPSI.

In yet another aspect of the multimodal-release composition, the SPSI comprises at least 1 wt % of a divalent cation, a trivalent cation, or a combination thereof and the SSPSI comprises at least 1 wt % of a monovalent cation. The SPSI may further comprise at least 1 wt % of a monovalent cation, as explained above. Additionally, the SSPSI may further at least 1 wt % of a divalent cation, a trivalent cation, or a combination thereof.

Examples of monovalent cations include, but are not limited to, monovalent sodium ($Na^+$), monovalent potassium ($K^+$), ammonium ($NH_4^+$), an alkylammonium ($RNH_3^+$, $R_2NH_2^+$, etc. where R is a C1-6 alkyl (straight or branched), proton ($H^+$), lithium ($Li^+$), monovalent copper ($Cu^+$), etc.

One will appreciate that the weight-amount of a monovalent cation is not without an upper bound. For instance, one will appreciate the weight-amount of monovalent cation will depend on the weight amount and total charge of, for example, phosphonate, such that a stoichiometric amount cationic species will be present in the SSPSI. Thus, if the polyphosphonate has a negative charge of 6, then the scale inhibitor comprises 6-mole equivalents of a monovalent cation, such that the mole ratio of monovalent cation to polyphosphonate is about 6. The exemplary calculations included herein may allow one to calculate readily the % weight of monovalent cation.

In one aspect, the multimodal-release composition for inhibiting scale in an industrial water system, each of the SPSI and SSPSI has a particle size of from about 20 to about 100, with specific values of about 20 mesh, about 30 mesh, about 35 mesh, about 40 mesh, about 45 mesh, about 50 mesh, about 60 mesh, about 80 mesh, and about 100 mesh.

Method for Inhibiting Scale Formation Using Multimodal-Release Composition

The multimodal-release composition disclosed herein may be included along with a proppant during hydraulic fracturing, including, for example in a horizontal well, or a vertical well.

Accordingly, another embodiment disclosed herein relates to a method for inhibiting scale formation in a subterranean formation, the method comprising mixing the multimodal-release composition disclosed herein with a stimulation composition comprising a stimulation fluid and optionally one or more proppants to form a stimulation mixture and injecting the stimulation mixture under pressure into hydraulically generated fractures of a wellbore.

As stated above, the presence or absence of one or more proppants may depend on the status of the well and that description may be applicable for the multimodal-release composition disclosed herein.

In one aspect, the stimulation composition comprises one or more proppants and the stimulation mixture of the method for inhibiting scale formation in a subterranean formation comprises from about 0.01% to about 5% of the combined weight of the SPSI and the SSPSI based on the weight of the proppant and all values in between including, for example, about 0.1%, about 1%, about 2%, about 3%, and about 4%.

In yet another aspect of the method for inhibiting scale formation in a subterranean formation, the mixture, in addition to the multimodal-release composition and the proppant, may further comprise one or more of a corrosion inhibitor, a paraffin inhibitor, a salt formation inhibitor, a gas hydrate inhibitor, an asphaltene inhibitor, an asphaltene dispersant, a defoamer, an oxidizer, an oxygen scavenger, a biocide, a foaming agent, an emulsion breaker, and a surfactant.

In another aspect, the stimulation mixture comprises (or consists of) from about 0.001 pptg to about 5 pptg of the combined amount of the SPSI and the SSPSI based on the volume of the stimulation fluid, including, for example, about 0.01 pptg, about 0.1 pptg, about 0.5 pptg, about 1 pptg, about 2 pptg, about 3 pptg, and about 4 pptg. In one aspect, the stimulation mixture comprises (or consists of) from about 0.01 pptg to about 1 pptg of the combined amount of the SPSI and the SSPSI based on the volume the volume of the stimulation fluid.

Another embodiment disclosed herein relates to a method for inhibiting scale formation, the method comprising mixing the multimodal-release composition disclosed herein with an aqueous fluid to obtain a scale inhibiting composition and adding the scale inhibiting composition to the system to inhibit scale formation on a surface of the system which is in contact with the fluid.

In one aspect, the scale inhibiting composition comprises (or consists of) from about 0.001 pptg to about 5 pptg of the combined amount of the SPSI and the SSPSI based on the volume of the stimulation fluid. In one aspect, the scale inhibiting composition comprises (or consists of) from about 0.01 pptg to about 1 pptg of the combined amount of the SPSI and the SSPSI based on the volume the volume of the stimulation fluid.

In one aspect of the method for inhibiting scale, the surface of the system is within a heat exchanger, a cooling tower, a pipeline, a water softener, a wastewater treatment system, a paper mill, a mining system, a geothermal system, a fluid cooling system, a water treatment system, a water purification system, a wastewater treatment system, a reverse osmosis membrane, an ultrafiltration system, a water storage system, or an ion exchanger.

In an aspect of the embodiments disclosed herein, the extended-release composition or the multimodal-release composition where each of the SPSI and the SSPSI may be substantially free of an inert material, where the inert material may be an inert support material (e.g., inorganic or organic), an inert coating material (e.g., inorganic or organic), or a combination thereof. Examples of inert support materials include, for example, diatomaceous earth, activated carbon, silica (e.g., silica particulate), precipitated silica, zeolite, ground walnut shells, Fuller's earth, a polymeric material, or an organic synthetic high molecular weight water-insoluble adsorbents. Examples of inert coating materials include, for example, a polyolefin, a polyester, a polyamide, a polycarbonate, a polyacetal, a polymelamine, a polyvinyl chloride, a polyvinylidene dichloride, a polyvinyl acetate, a polyvinyl ester, a polyacrylic acid, a bisphenol, an isocyanate, or blends thereof, including, for example, ethylene vinyl acetate, polylactic acid, a product of phthalic anhydride and ethylene vinyl acetate, a mixture comprising ethylene vinyl acetate and a plasticizer (e.g., dioctyl phthalate).

In other aspects of the embodiments disclosed herein, it may be appreciated that the extended-release composition or multimodal-release composition includes only the recited elements. Accordingly, one will appreciate that the expression "comprising" (or its equivalent) may be replaced with "consisting of" (or its equivalent), as appropriate.

EXAMPLES

The following exemplified embodiments illustrate aspects of the compositions disclosed herein and should not be limiting on the subject matter claimed herein.

Figure 1:
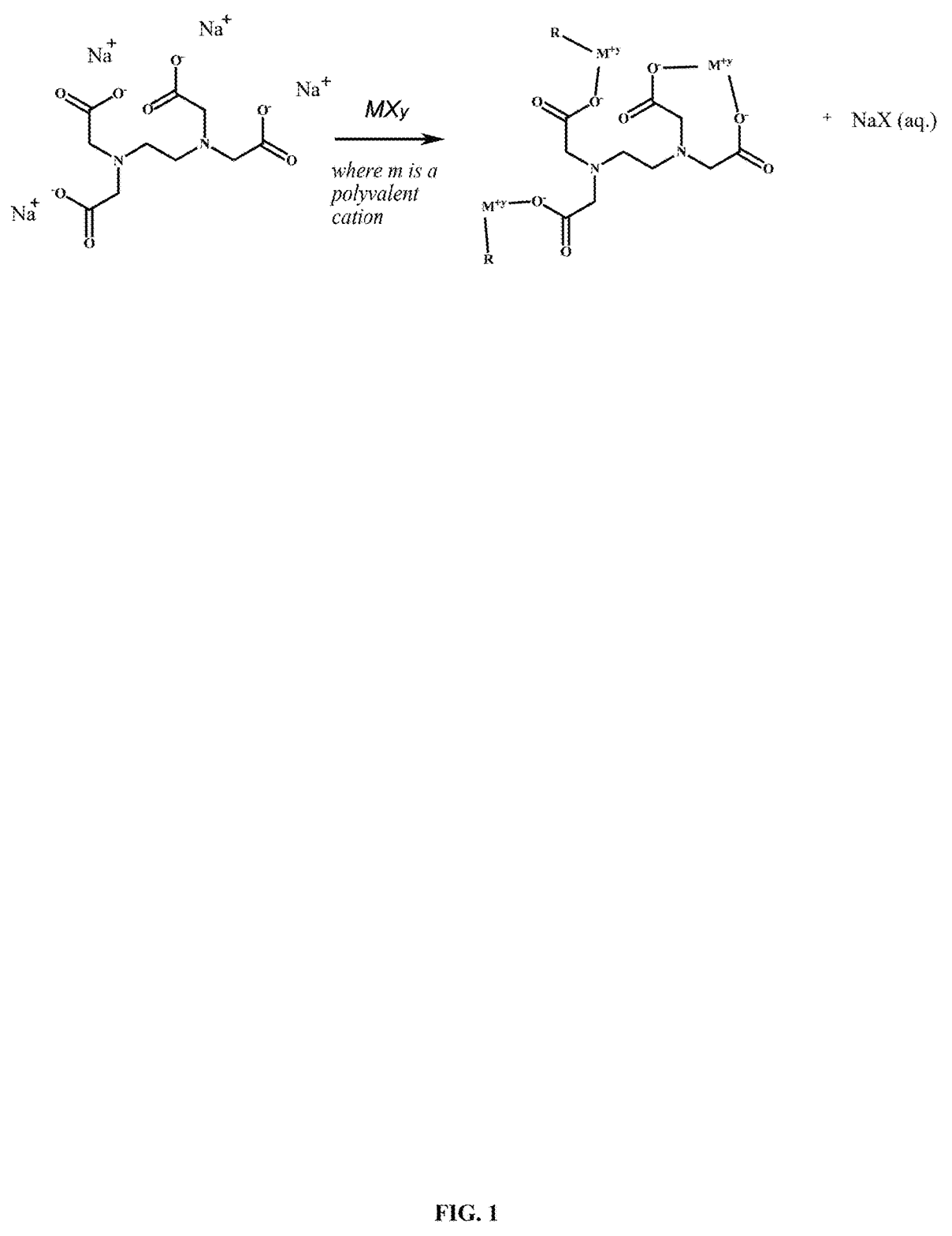

As shown in FIG. 1, scale inhibitors disclosed herein may be readily prepared by reacting soluble forms of the actives (e.g., polycarboxylates, polyphosphonates, and the like) with soluble solutions of polyvalent metal cations (e.g., $MgCl_2$, $CaCl_2$, etc.). As a point of reference, FIG. 1 includes an "R" moiety, which may be a polycarboxylate, a polyphosphonate, and the like). The active may be present in acid form, or in soluble salt form where monovalent cations balance the anionic charges on the active ingredient. As the protons or monovalent salts exchange with the polyvalent cations in solution via the familiar process of cation metathesis, the organic salts become insoluble and precipitate from solution. These salts may be isolated via filtration, centrifugation or other suitable methods, washed to remove residuals salts (e.g., NaCl, KCl, etc.), and dried to isolate the desired composition.

The stoichiometry of the resulting compositions (i.e., ratio of polyvalent cation "M" to anionic moiety on the active ingredient) may vary and will be driven by the solubility of the final composition and the conditions used to prepare the product (e.g., concentrations and rates of addition, temperature, mixing conditions, etc.). Cation metathesis may not proceed completely prior to precipitation, resulting in a mixed salt product, and all "partially" metathesized variations of the product, while still sparingly soluble, are claimed herein.

Proof-of-concept experiments were conducted by preparing Ca and Mg salts of both ATMP and DTPMP using the K salts as intermediates.

As a point of reference, a calcium salt of aminotrimethylenephosphononate acid (viz., calcium-ATMP) was prepared by dissolving about 59.8 grams of aminotrimethylenephosphonic acid (ATMP, 6419-19-8) in water and adding about 67.3 grams (~6-mole equivalents) of potassium hydroxide (KOH, as 85% w/v in water) to provide the potassium salt of ATMP. To this solution was added about 113.2 g of $CaCl_2 \cdot 6H_2O$ (about 5-mole equivalents of $Ca^{2+}$) and about 180 g of water while maintaining the pH at about 6-7 and the temperature at about 65° C. The reaction may proceed at any suitable temperature that ranges from room temperature to about 120° C. (or higher in a closed system). The calcium-salt of ATMP precipitated from solution and was collected by filtration, washed with water, and dried. Similar methods were used to prepare calcium-salt of DTPMP, as well as magnesium-salts of ATMP and DTPMP.

Prolonged dissolution studies were conducted by placing an amount of the salt (usually≈1 g) in a small, water-permeable pouch, immersing the pouch in a fixed volume of deionized water (usually ~100 mL), heating the water to a target temperature (usually 65° C., but ranging from room temperature to 120° C.), and monitoring the weight loss of the pouch as a function of time. The results of this initial study are shown in FIG. 2. Based on results presented herein, the K-salts of the phosphonates were readily soluble (data not shown), but upon conversion to the Ca- or Mg-salt, the solubility of the phosphonate decreased significantly. After 3-weeks at elevated temperature, only 35-60% of the samples had dissolved. The Ca-salts were found to dissolve more slowly than the Mg-salts. There was not a significant difference in dissolution rate between the two phosphonates.

Figure 3:
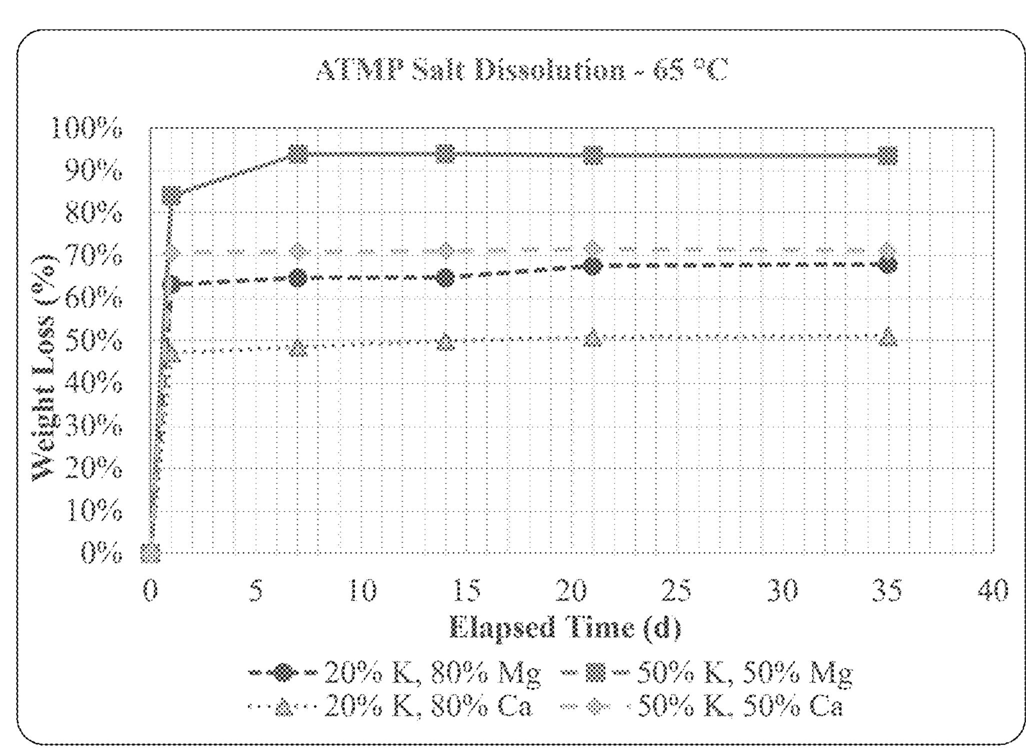
FIG. 3. ATMP dissolution in deionized water (65° C.). Salt blends were prepared with varying amounts of monovalent cations ($K^+$) or divalent cations ($Ca^{2+}$ or $Mg^{2+}$) in order to modify the release rate of the active phosphonate.
Figure 4:
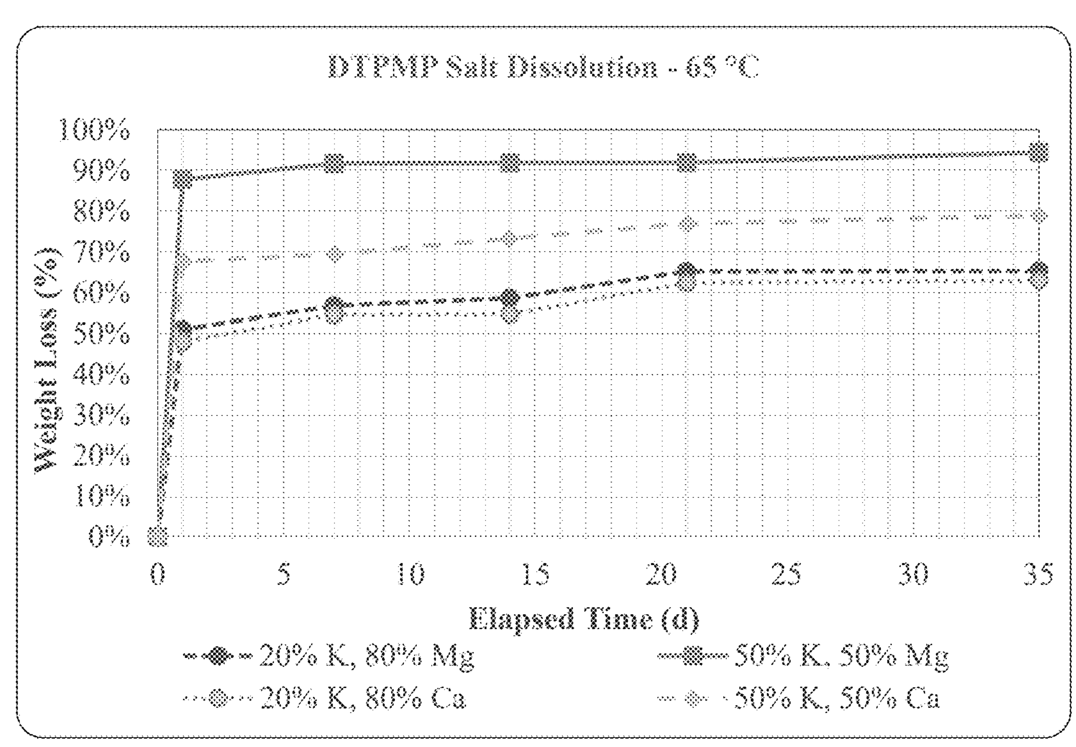
FIG. 4. DTPMP dissolution in deionized water (65° C.). Salt blends were prepared with varying amounts of monovalent cations ($K^+$) or divalent cations ($Ca^{2+}$ or $Mg^{2+}$) in order to modify the release rate of the active phosphonate.

It is possible to control the release rate of the scale inhibitor by manufacture of a multimodal-release composition. Variation of the amount of monovalent vs. divalent cation will have a direct impact on how quickly the phosphonate dissolves. This was demonstrated for both ATMP and DTPMP, as shown in FIG. 3 and FIG. 4. The K-, Mg-, and Ca-salts of each phosphonate were prepared independently and then blended according to the ratios shown in FIGS. 3-4. The results presented herein show that salt blends rich in divalent salts dissolved more slowly than the salt blends having greater amounts of monovalent salts.

Moreover, consistent with the data shown in FIG. 2, it was observed that Ca-salts dissolved more slowly than the Mg salts. Thus, collectively, dissolution rate can be controlled such that it is possible to speed up or slow down solely by modifying the cation composition.

Figure 5:
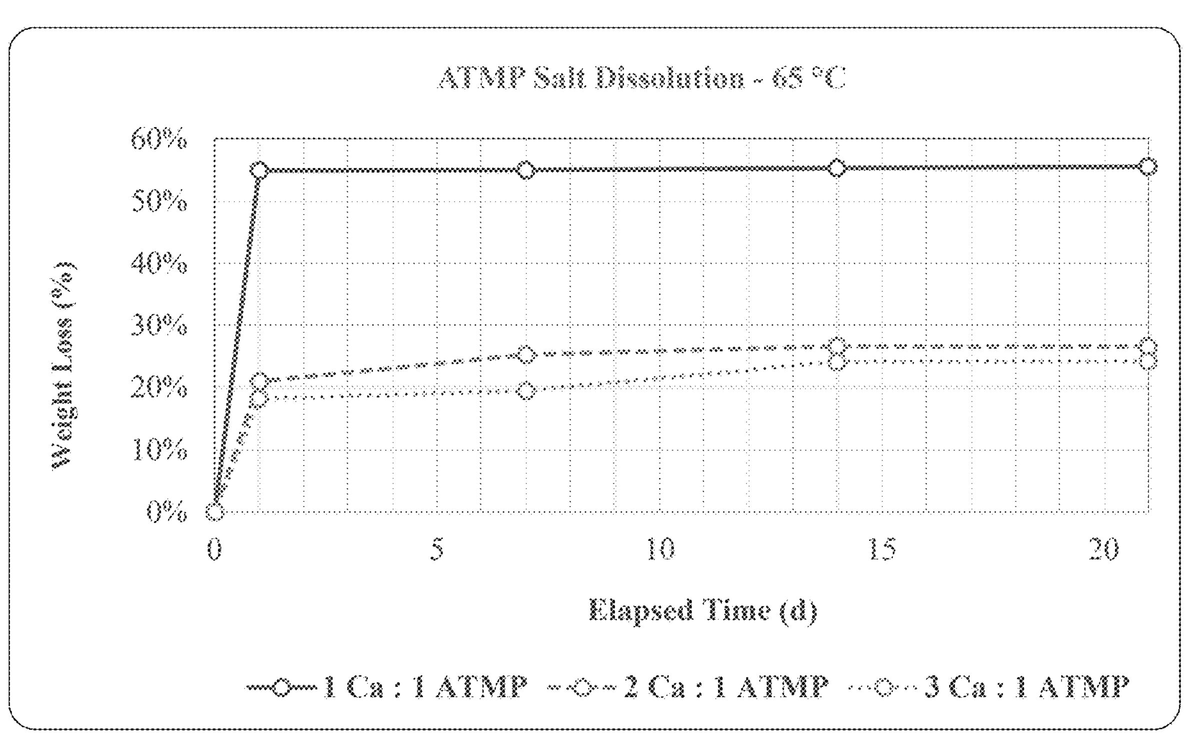
FIG. 5. Dissolution of Ca-ATMP salts prepared with varying Ca-to-ATMP stoichiometries.

During this work, it was discovered that dissolution of the salts is dependent on the stoichiometry of the divalent cation to the anionic phosphonate. As reported in previous literature studies of ATMP (see Tantayakom), the pH of the phosphonate solution (prior to introduction of a divalent cation) will determine whether mono-, di-, or tri-substituted salt is preferentially produced. At a pH of about 1.5, a mono-substituted salt is produced due to the relatively minimal extent of deprotonation of the phosphonate moieties, At a pH of about 4, a di-substituted salt is produced, and at a pH of about 7, a tri-substituted salt is produced. As shown in FIG. 5, this variation in substitution has a significant impact on the dissolution behavior of the resulting salts. The mono-substituted salt dissolves faster than the di-substituted salt, which dissolves faster than the tri-substituted salt. Thus, in addition to using the chemical identity of the cation to control dissolution behavior, the degree of substitution provides another lever for modifying the solubility of an anionic scale inhibitor.

Cited Information

Gao et al., *High Return Performance of Calcium Phosphonate (Ca-DTPMP) Colloidal Inhibitors for Squeeze Treatment in Shale Formations*, Front. Mater. (2020) 7:285 (DOI: 10.3389/fmats.2020.00285).

Kan et al., *Formation of Two Calcium Diethylenetriaminepentakis(methylene phosphonic acid) Precipitates and Their Physical Chemical Properties*, Langmuir (1994) 10:1450-1455.

Kuhn et al., *The influence of selected bivalent metal ions on the photolysis of diethylenetriamine penta(methylenephosphonic acid)*, Chemosphre (2018) 210:726-733 (DOI: 10.1016/j.chemosphere.2018.07.033).

Oddo et al. *The solubility and stoichiometry of calcium-diethylenetriaminepenta(methylene phosphonate) at 70° C. in brine solutions at* 4. 7 *and* 5.0 *pH*, Applied Geochemistry. (1990) 5:527-532.

Pairat et al., *Precipitation and dissolution of calcium-ATMP precipitates for the inhibition of scale formation in porous media*, Langmuir (1997) 13 (6): 1791-1798.

Reinhardt et al., *Batch Studies of Phosphonate and Phosphate Adsorption on Granular Ferric Hydroxide (GFH) with Membrane Concentrate and Its Synthetic Replicas*, Molecules (2020) 25, 5202 (doi: 10.3390/molecules25215202).

Tantayakom et al., *Study of Ca-ATMP Precipitation in the Presence of Magnesium Ion*, Langmuir (2004) 20(6): 2220-2226.

U.S. Patent Application Publication No. 2013/0123149 A1, Polyelectrolyte Complexes for Oil and Gas Applications, to Berkland et al.

U.S. Pat. No. 3,272,588 A, Method of inhibiting corrosion with slowly soluble phosphate glasses, to Fuchs, R. J.

U.S. Pat. No. 3,338,670 A, Slowly soluble phosphate glasses, to Fuchs, R. J.

U.S. Pat. No. 8,664,168 B2, Method of using composites in the treatment of wells, to Steiner, W. H.

U.S. Pat. No. 8,822,390 B2, Scale inhibitor, to Heath et al.

U.S. Pat. No. 9,878,960 B2, Slow and fast release fertilizer composition and methods for making same, to Clark et al.

U.S. Pat. No. 9,970,265 B2, Multi-functional surfactant complexes for use in subterranean formations, to Xu et al.

U.S. Pat. No. 10,253,244 B2, Scale-inhibiting cocrystals for treatment of a subterranean formation, to Holtsclaw et al.

U.S. Pat. No. 10,611,953 B2, Controlled release of well treatment agents into oil wells, to Patil et al.

U.S. Pat. No. 11,142,680 B2, Controlled release solid scale inhibitors, to Dreyer et al.

Vazquez et al., *Automatic optimization of oil field scale inhibitor squeeze treatment designs*, J. Pet. Sci. Eng. (2016) 147:302-307 (DOI: 10.1016/j.petrol.2016.06.025).

Zhang et al., *Mechanistic understanding of calcium-phosphonate solid dissolution and scale inhibitor return behavior in oilfield reservoir: formation of middle phase*, Phys. Chem. Chem. Phys. (2016) 18:21458 (DOI: 10.1039/c6cp03148j).

Zhang, P., *Review of Synthesis and Evaluation of Inhibitor Nanomaterials for Oilfield Mineral Scale Control*, Front. Chem. (2020) 8:576055 (DOI: 10.3389/fchem.2020.576055) ("Zhang (2020)").

The information cited herein is incorporated by reference in its entirety to the extent necessary. If there is a difference in meaning between the incorporated terms and the terms disclosed herein, the meaning of the terms disclosed herein will control.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

The invention claimed is:

1. A multimodal-release composition for inhibiting scale in an industrial water system comprising:
 an extended-release composition, wherein the extended-release composition comprises:
  a solid, particulate scale inhibitor comprising:
   a ligand component comprising at least one of a phosphonate, a carboxylate, or a combination thereof; and
   a multivalent cation comprising at least one of a divalent cation, a trivalent cation, or a combination thereof, and
 a second solid, particulate scale inhibitor comprising:
  a second ligand component comprising at least one of a phosphonate, a carboxylate, or a combination thereof; and
  a monovalent cation,
 wherein the extended-release composition and the second solid, particulate scale inhibitor are present in a weight ratio of from about 10:1 to about 1:10.

2. The multimodal-release composition of claim 1, wherein the solid, particulate scale inhibitor has a water solubility of about 10,000 or less compared to the second solid, particulate scale inhibitor.

3. The multimodal-release composition of claim 1, wherein:
 the solid, particulate scale inhibitor comprises at least 1 wt % of the multivalent cation; and
 the second solid, particulate scale inhibitor comprises at least 1 wt % of a monovalent cation.

4. The multimodal-release composition of claim 1, wherein the divalent cation comprises at least one of a calcium or magnesium.

5. The multimodal-release composition of claim 1, wherein the ligand component comprises a salt-form selected from a group consisting of 1-hydroxyethylidene-(1,1-diphosphonic acid) (HEDP); aminobis(methylenephosphonic acid) (ABMP); methyliminobis(methylenephosphonic acid) (MIBMP); aminotri-methylenephosphonic acid (ATMP); diethylenetriamine-penta(methylenephosphonic acid) (DTPMP); 1 ethylenediaminetetra(methylene phosphonic acid) (EDTMP); bis(hexamethylenetriaminepenta (methylenephosphonic acid)) (BHMTPMP); citric acid; isocitric acid; aconitic acid; 1,3,4-propanetricarboxylic acid; dihydroxymaleic acid; 1,2-diaminocyclohexane-N,N,N',N'-tetraacetic acid (DCyTA); ethylenediaminetetraacetic acid (EDTA); diethylenetriaminepentaacetic acid (DETPA); nitrilotriacetic acid (NTA); iminodiacetic acid (IDA); hydroxyethylethylenediaminotriacetic acid (HEDTA); ethylenediamine-N,N'-disuccinic acid (EDDS); methyglycine diacetic acid (MGDA); (2-hydroxyethyl)iminodiacetic acid (HEIDA); glutamic acid-N,N-diacetic acid (GLDA); ethylenediaminedi-o-hydroxyphenylacetic acid (EDDHA); N-methyliminodiacetic acid (MIDA); iminodisuccinic acid (IDS); 1,2-diaminopropane-N,N,N',N'-tetraacetic acid (MeEDTA); N-(2-acetamido)iminodiacetic acid (ADA); N-(2-carboxyethyl)iminodiacetic acid; L-aspartic acid-N,N-di(acetic acid) (ASDA); N-(carboxymethyl)-L-aspartic acid; strombine; hydroxyiminodisuccinic acid; N-(carboxymethyl) aspartic acid; N-bis[2-(1,2-dicarboxyethoxy) ethyl] glycine; N,N'-1,3-propanediylbis (aspartic acid); 1,6-hexamethylenediamine N,N'-disuccinic acid; 2,2',2", [nitrilotris (2,1-ethanediyloxy)] tris [butanedioic acid]; N-(carboxymethyl)-N-(hydroxymethyl) glycine; 1,3-diamino-2-hydroxypropane-N,N'-disuccinic acid; N-(2-carboxyethyl) aspartic acid; N,N-bis[2-(1,2-dicarboxyethoxy)ethyl] aspartic acid; N,N'-(iminodi-2,1-ethanediyl)bis(aspartic acid); 2,16-bis(carboxymethyl)-3,6,9,12,15-pentaazaheptadecanedioic acid; 3,6,9,12-tetraazatetradecane-1,2,13,14-tetracarboxylic acid; N,N'-(1-methyl-1,2-ethanediyl) bis(aspartic acid); N,N-bis(carboxymethyl)-3-sulfo-L-alanine; N-(carboxymethyl)-3-sulfo-L-alanine; 2,13-bis(carboxymethyl)-6,9-dioxa-3,12-diazatetradecanedioic acid; N-(3-carboxy-3-hydroxy-1-oxopropyl)-L-aspartic acid; 2,2'-[[(1-carboxyethyl)imino] bis(2,1-ethanediyloxy)] bis [butanedioic acid]; N-[(1S)-1-carboxy-2-hydroxyethyl]-3-hydroxyaspartic acid; and N,N'-cyclohexanediylbis(aspartic acid); 2-carboxyethyl phosphonic acid (CEPA); 2-hydroxyphosphonocarboxylic acid (HPAA); N,N-bis(phosphonomethyl)glycine (BPMG); N-(phosphonomethyl) iminodiacetic acid (PMIDA); phosphonobutanetricarboxylic acid (PBTC); 2-phosphonobutane-1,2,4-tricarboxylic acid (PBTC); 2-hydroxy phosphonoacetic acid (HPAA); (2-phosphono butane-1,2,4-tricarboxylic acid (PBTCA); N-(Phosphonomethyl) glycine; N-(phosphonomethyl) iminodiacetic acid (H4PMIDA); 1,4,7-triazacyclononane-N,N',N"-trimethylene phosphonic acid (H6NOTP); 1,4,7-triazacyclononane-N-methylenephosphonic acid-N',N"-dimethylenecarboxylic acid (H4NO2AP); 1,4,7-triazacyclononane-N,N'-bis(methylene-phosphonic acid)-N"-methylene carboxylic acid (H5NOA2P); polyvinylphosphonic acid; polyacrylic acid; polymethacrylic acid; polyphosphinocarboxylic acid; aminoethylethanolamine (AEEA) phosphonic acid or its salts thereof; or a combination thereof.

6. The multimodal-release composition of claim 1, wherein the solid, particulate scale inhibitor has a particle size between about 150 microns and about 500 microns.

7. The multimodal-release composition of claim 1, wherein the solid, particulate scale inhibitor further comprises a monovalent cation.

8. The multimodal-release composition of claim 1, wherein the second solid, particulate scale inhibitor has a water solubility greater than about 10,000 ppm.

9. The multimodal-release composition of claim 1, wherein the first solid, particulate scale inhibitor dissolves in water at a rate at least 1,000 times slower than the second solid, particulate scale inhibitor under identical aqueous conditions.

10. The multimodal-release composition of claim 1, wherein the monovalent cation of the second solid, particulate scale inhibitor is selected from a group consisting of monovalent sodium ($Na^+$), monovalent potassium ($K^+$), ammonium ($NH_4^+$), an alkylammonium ($RNH_3^+$, $R_2NH_2^+$, $R_3NH^+$ or $R_4N_2^+$, where R is a C1-6 alkyl (straight or branched), proton ($H^+$), lithium ($Li^+$), or monovalent copper ($Cu^+$).

11. The multimodal-release composition of claim 1, wherein the multimodal-release composition further comprises one or more proppants.

12. A method of inhibiting scale formation in a subterranean formation, the method comprising:
 forming a multimodal-release composition comprising:
  a extended-release composition comprising:
   a solid, particulate scale inhibitor comprising:
    a ligand component comprising at least one of a phosphonate, a carboxylate, or a combination thereof; and a multivalent cation comprising at least one of a divalent cation, a trivalent cation, or a combination thereof; and a second solid, particulate scale inhibitor comprising:

a second ligand component comprising at least one of a phosphonate, a carboxylate, or a combination thereof; and a monovalent cation, wherein the extended-release composition and the second solid, particulate scale inhibitor are present in a weight ratio of from about 10:1 to about 1:10;

mixing the multimodal-release composition with a stimulation composition comprising a stimulation fluid and optionally one or more proppants to form a stimulation mixture; and injecting the stimulation mixture under pressure into hydraulically generated fractures of a wellbore.

13. The method of claim 12, wherein forming the multimodal-release composition comprises: reacting a readily aqueous soluble phosphonate, carboxylate, or a combination thereof with a readily aqueous soluble metal salt comprising a divalent cation, a trivalent cation, or a combination thereof to obtain a solid scale inhibitor.

14. The method of claim 12, wherein forming the multimodal-release composition comprises: grinding a solid scale inhibitor to obtain the solid, particulate scale inhibitor having a particle size of at least about 100 mesh.

15. The method of claim 12, wherein the stimulation composition comprises one or more proppants and the stimulation mixture comprises from about 0.01% to about 1% of the solid, particulate scale inhibitor based on the weight of the one or more proppants.

16. The method of claim 12, wherein the stimulation mixture comprises from about 0.001 pptg to about 5 pptg of the solid, particulate scale inhibitor based on the volume of the stimulation fluid.

17. A method of inhibiting scale formation in an industrial water system, said method comprising:

forming a multimodal-release composition comprising:

a extended-release composition comprising:

a solid, particulate scale inhibitor comprising:

a ligand component comprising at least one of a phosphonate, a carboxylate, or a combination thereof; and a multivalent cation comprising at least one of a divalent cation, a trivalent cation, or a combination thereof; and a second solid, particulate scale inhibitor comprising:

a second ligand component comprising at least one of a phosphonate, a carboxylate, or a combination thereof; and a monovalent cation, wherein the extended-release composition and the second solid, particulate scale inhibitor are present in a weight ratio of from about 10:1 to about 1:10;

mixing the multimodal-release composition with an aqueous fluid to obtain a scale inhibiting composition; and adding the scale inhibiting composition to the system to inhibit scale formation on a surface of the system which is in contact with the fluid.

18. The method of claim 17, wherein the scale inhibiting composition comprises from about 0.001 pptg to about 5 pptg of the solid, particulate scale inhibitor based on the volume of the of the aqueous fluid.

19. The method of claim 17, wherein the surface is within a heat exchanger, a cooling tower, a pipeline, a water softener, a wastewater treatment system, a paper mill, a mining system, a geothermal system, a fluid cooling system, a water treatment system, a water purification system, a wastewater treatment system, a reverse osmosis membrane, an ultrafiltration system, a water storage system, or an ion exchanger.

* * * * *